(12) United States Patent
Pacheco et al.

(10) Patent No.: US 7,632,853 B2
(45) Date of Patent: Dec. 15, 2009

(54) SOLUBLE, STABLE AND CONCENTRATED PHARMACEUTICAL COMPOSITION COMPROMISING RITONAVIR AND PROCESS FOR PREPARING THEREOF

(75) Inventors: Ogari Pacheco, Itapira (BR); Elisa Rusoo, Itapira (BR); Valter Russo, Itapira (BR)

(73) Assignee: Cristalia Produtos Quimicos Farmaceuticos LTDA, Itapira (BR)

( * ) Notice: Subject to any disclaimer, the term of this patent is extended or adjusted under 35 U.S.C. 154(b) by 314 days.

(21) Appl. No.: 10/517,453

(22) PCT Filed: Jun. 12, 2003

(86) PCT No.: PCT/BR03/00076

§ 371 (c)(1),
(2), (4) Date: Dec. 9, 2004

(87) PCT Pub. No.: WO03/105826

PCT Pub. Date: Dec. 24, 2003

(65) Prior Publication Data

US 2005/0250764 A1 Nov. 10, 2005

(30) Foreign Application Priority Data

Jun. 12, 2002 (BR) .................................... 0202252

(51) Int. Cl.
*A01N 43/78* (2006.01)
*A61K 31/425* (2006.01)

(52) U.S. Cl. ...................................... 514/365; 424/400
(58) Field of Classification Search .................. 514/310, 514/365; 424/400
See application file for complete search history.

(56) References Cited

U.S. PATENT DOCUMENTS 6,008,228 A * 12/1999 Bailey et al. ................. 514/307
6,232,333 B1 * 5/2001 Lipari et al. ................. 514/365

FOREIGN PATENT DOCUMENTS

WO WO-96/39142 B 12/1996
WO WO 98/57648 A1 12/1998

OTHER PUBLICATIONS

Rowe et al., Handbook of Pharmaceutical Excipients, 2006, Pharmaceutical Press, Fifth Edition, pp. 545-550 (Polyethylene Glycol).*
Wikipedia, http://en.wikipedia.org/wiki/Vacuum-distillation, pp. 1-2.*
Wikipedia, http://en.wikipedia.org/wiki/Distillation, pp. 1-11.*
CU Boulder Organic Chemistry Undergrauate Courses, Lab Techniques, http://we.archive.or/web/20010419135852/orgchem.colorado.edu/handbksupport/dist/dist.html, pp. 1-2.*
CUBoulder Organic Chemistry Undergraduate Courses, Lab Techniques, http: //web.archive.org/web/20020417050311/orgchem.colorado.edu/hndbksupport/solvremoval/solvremoval.html, pp. 1-4.*
L. Eldred, The Hopkins HIV Report, "Adherence in the Era of Protease Inhibitors", 1997.
F.M. Hecht et al., Abstract of Presentation from the 5th Conference on Retroviruses and Opportunistic Infections, Feb. 1-5, 1998, Chicago, IL.
M. Chesney et al., "Adherence to Combination Therapy in AIDS Clinical Trials (1997)", presented at the Annual Meeting of the AIDS Clinical Trials Group, Jul. 1997, Washington, D.C.
J. Walsh et al., Abstract of presentation "Adherence to proteinase inhibitor based highly effective antiretroviral therapy (HEART)" from 12th International AIDS Conference held in Geneva, Switzerland, Jun. 28-Jul. 3, 1998.

* cited by examiner

*Primary Examiner*—Frederick Krass
*Assistant Examiner*—Gigi Huang
(74) *Attorney, Agent, or Firm*—Birch, Stewart, Kolasch & Birch, LLP

(57) ABSTRACT

The present invention describes a soluble stable pharmaceutical composition for the administration of HIV protease inhibitors. More specifically the composition comprises a solution of an HIV protease inhibitor in a combination of suitable pharmaceutical organic solvents, a surfactant and a bioavailability enhancer. It is also described a process for the obtainment of concentrated pharmaceutical compositions used in the administration of HIV protease inhibitors compounds. The composition of the present invention is suitable for the preparation of oral solutions for the administration of active drugs and for the encapsulation in hard gelatin capsules or soft gelatin capsules.

14 Claims, No Drawings

SOLUBLE, STABLE AND CONCENTRATED PHARMACEUTICAL COMPOSITION COMPROMISING RITONAVIR AND PROCESS FOR PREPARING THEREOF

The present application is a National Stage entry of PCT/BR2003/00076 filed on Jun. 12, 2003, and priority is also claimed to Brazil patent application PI0202252-4 filed Jun. 12, 2002 under 35 U.S.C. § 119.

The present invention describes a soluble stable pharmaceutical composition for the administration of HIV protease inhibitors. More specifically the composition comprises a solution of an HIV protease inhibitor in a combination of suitable pharmaceutical organic solvents, a surfactant and a bioavailability enhancer. It is also described a process for the obtainment of concentrated pharmaceutical compositions used in the administration of HIV protease inhibitors compounds. The composition of the present invention is suitable for the preparation of oral solutions for the administration of active drugs and for the encapsulation in hard gelatin capsules or soft gelatin capsules.

AIDS treatment ("Acquired Immunodeficiency Syndrome") employs medicines which have to be administrated daily, most of them in an elevated dosage and which treatment preferably should not be interrupted even a day for the rest of the infected individuals lives.

One of the main concerns from health professionals dealing with the treatment of the affected individuals by AIDS is the possibility of virus resistance development, an usual occurrence when the active drug does not reach the target tissues in a minimum amount necessary to eradication or complete inactivation of the infectious agent. Drug resistance is without doubt one of the biggest problems that can arouse during the treatment of diseases caused by infectious agents and the efforts to avoid it are frequent.

A drug must comply several requirements in order to be considerate adequate to therapeutic usage. Among them, it has to present therapeutic efficacy and for that it must present adequate bioabsorption and bioavailability characteristics, it should present an administration route less invasive as possible for don't submitting patients to painful or uncomfortable procedures during its administration, and the most important issue is that the drug must incentive and elevate adherence of the patient to the treatment.

Adherence is defined as an act, action or quality of being consistent with the administration of the prescribed medicines. Adherence becomes more important as longer therapy duration.

The success of AIDS treatment with antiretroviral drugs depends mainly upon the patient adherence to the therapy itself, consisting this therapy in the administration of significant amounts of different medicines several times a day.

Accordingly with the final report named "Avaliação da Aderência ao Tratamento por Anti-retrovirais em Usuários de Ambulatórios do Sistema Público de Assistência à AIDS no Estado de São Paulo" (a report evaluating the adherence of patients to antiretroviral therapy in the State of São Paulo-Brazil), non-adherence to new AIDS medicines (antiretroviral mainly and protease inhibitors in particular) is considered one of the most threatening danger to the effectiveness of the treatment, in an individual level, and for the dissemination of virus-resistance, in a collective level. That's because new AIDS administration therapies seems to request from the adherent a complex integration between knowledge, ability and acceptation, besides other important issues related to environment and to the health care. The report discusses the matter of non-adherence being an universal phenomenon in a certain rate, occurring either in rich and poor countries, even in cases of life threatening diseases.

Adherence to anti-retroviral therapy is a motive of apprehension among health professionals, once researches about this issue show that it is very low even in rich countries where it reaches only 70% of the patients under treatment (Walsh J., Dalton M., Gill J., Wilkinson D. Burgess A.P., Gazzard B.G.—Adherence to protease inhibitor based highly effective anti-retroviral therapy (HAART) in 12th World Aids Conference, Geneva 1998. Abstracts; Hecht F.M., Colfax G., Swanson M., Chesney M.A.—Adhererence and effectiveness of protease inhibitors in clinical practice in 5th Conf. Retrovir. Oppor. Infect., San Francisco, 1998 Abstracts, e Eldred L.—Adherence in the era of protease inhibitors—John Hopkins AIDS Service). This percentage is considered very low for a fatal disease, especially considering that these studies only deal with the adherence to the recommended quantity of medicines.

In particular one of the components from the anti-aids cocktail, corresponds to an especial class of drugs acting by inhibiting the retroviral protease, known as protease inhibitors. Protease inhibitors are substances with high molecular weight, with a lipophilic character, slight or very slight soluble in water and usually present low absorption and low bioavailability when therapeutically administered on the solid form. Due to those characteristics, elevated and frequent dosages are necessary to maintenance of an ideal therapeutic circulating level of the drug on the organism.

These physicochemical characteristics of these protease inhibitors make difficult the development of concentrate pharmaceutical compositions for the administration of these drugs. This is due to the low solubility of these substances in the pharmaceutical compositions proposed until the present moment.

As pointed out earlier, protease inhibitors present low absorption and bioavailability if administered in the solid state. The administration of these substances by means of syrups and oral solutions as far as the present moment are not well accepted by patients because its bad taste, which is very difficult to mask by the addition of suitable excipients.

Another difficulty related to the administration of these substances as an oral solution involves the manipulation of administration devices, procedure that inhibits patients to follow the administration regime once in non-private places, avoiding the natural curiosity and prejudice inherent to the condition established by the disease.

It was recently developed compositions in order to proportionate a discrete and adequate administration way, which consists in the administration of soft gelatin capsules, comprising the liquid composition surrounded by a thin elastic pellicle of gelatin. Due the elastic characteristic proportionate a smoother ingestion, the acceptance of them is higher to the conventional tablets or the hard gelatin capsules.

Other great importance of this kind of composition relies on the possibility of administering drugs in a liquid form, where the active pharmaceutical ingredient is dissolved in a solution. Once ingested, the capsule breaches liberating its contend homogeneously in the gastrointestinal tract, which as a liquid it does not need to be dissolved in order to be absorbed by the organism.

Although the pharmaceutical presentations had involved dealing with the need of supply these drugs in a soluble form and in a better and acceptable presentation, the final presentation of these compositions shows little adequacy for the therapeutic administration of these drugs. Some factors explain this little adequacy: the capsules present large dimensions, low concentration of the drug and the necessity of raised daily doses leads to an oral administration of a large number of capsules for each dose taken by the patients.

These factors are negative in the view of the adherence of the patients to the therapy. The large dimensions of these capsules may be an important and an interfering factor if we consider the ability of ingestion by patients with some infections in the gastrointestinal tract and the necessity to ingest many capsules for each dosage.

Among the protease inhibitors actually in therapeutic use the 5S-(5R*,8R*,10R*,11R*)]-10-hydroxy-2-methyl-5-(1-methylethyl)-1-[2-(1-methylethyl)-4-thyazolyl]-3,6-dioxo-8,11-bis(phenylmethyl)-2,4,7,12-tetraazatridecan-13-oic acid 5-thiazolylmethyl ester, known as ritonavir, presents some properties which interfere in the development of concentrate compositions for the therapeutic administrations. This compound presents polymorphism and has polymorphic crystalline forms with markedly differences on solubility.

This difference in the solubility among these polymorphic forms explains the discontinuation of the composition initially commercialized, which presented along the years a crescent quantity of crystals of the less soluble polymorfic form of ritonavir, this fact compromised the efficacy of this drug in the suppression of the human immunodeficiency virus-HIV. This commercial composition was removed from the marked because of the danger in the development of virus resistance for this drug caused by the low bioavailability of this crystalline form and was substituted by the oral solution in which this problem could be detected from visual inspection of the composition by the patients, looking for crystals which can't be dissolved by manual agitation of the bottle.

The exchange of the capsules for the oral solution was largely criticized and show low acceptance by patients, which complain about its awkward metallic taste which remains many hours after the dosage, suppressing the appetite already compromised by the illness.

The solution for this problem of crystallization of the less soluble polymorphic form was the development of a new composition, which inhibits this crystallization. This new composition was developed to be taken in the form of soft gelatin capsules. Despite this new composition had suppress the crystallization of the less soluble polymorphic form, it shows some disadvantages, among others, the low physicochemical stability, the low concentration of the capsules leading the patients to ingest many capsules in each dosage, the large dimensions of the capsules making difficult the swallow by the patients, mainly the elder's, children's and weak patients or patients with some infections of the digestive tract with the compromise of the buccal cavity and throat.

These aspects leads to the development of a liquid composition more adequate for the administration of ritonavir, which presents: sufficient stability to be storage at room temperature, may be prepared at raised concentrations of the drug to reduce the number of capsules ingested by the patients in each dosage, presents great inhibition of the crystallization of the less soluble polymorfic form and may be ingested in the form of oral solution or, soft or hard gelatin capsules in reduced size to facilitate the ingestion by the patients, mainly the elder's, the children's and weaker patients.

Some references describe pharmaceutical compositions for the administration of ritonavir.

The application WO 98/22106 describes the actual and commercially available pharmaceutical composition, which presents a fatty acid as a pharmaceutical acceptable organic solvent and pharmaceutical acceptable tensoactive compound. Despite the authors proclaim the stability of this composition at room temperature and, their examples are focused in the attainment of concentrated capsules (200 mg/capsule), the marketed form has significant differences. The marketed composition consists in soft gelatin capsules in the concentration of 100 mg for capsule. The capsules have an average weight of 1,000 mg and this means a concentration of ritonavir as 10% of the final weight of the capsule. This choice for the final commercial composition indicates the inefficacious of this composition to inhibit the precipitation of ritonavir in a concentration of 200 mg/gram of the composition (200 mg/capsule). As consequence these capsules are very voluminous making difficult the ingestion and this low concentration led the patients to swallow a great number of capsules daily to attain the effective dosage of this drug. Beyond this factor, the label of this commercial composition indicates that it must be stored under refrigeration until its final use, when it may be stored at room temperature in a maximum period of a month. This warning denounces the lack of the physicochemical stability of these composition at ambient temperature and may lead again to a favorable condition where the precipitation of the less soluble polymorfic form will occur, just the same occurrence described before for the first composition which was obligatorily stored under refrigeration.

The application WO 96/39142 describes a liquid composition for the administration of several protease inhibitors, among them ritonavir, employing a mixture of mono and diglycerides of $C_8$-$C_{10}$ saturated fatty acids as organic solvent. Despite the inclusion of ritonavir in this document, the examples described compositions only for saquinavir. Experimentally, this composition is inadequate to supply stable composition of ritonavir, mainly if we consider compositions having high concentrations, for example 200 mg/1g of the composition. Another negative aspect for this composition is the high temperature needed for the complete dissolution of ritonavir in the described excipients which may lead to a thermal degradation of this drug.

The document WO 98/57648 describes several methods to increase the bioavailability of polymorphic crystalline forms for many compounds including ritonavir. This approach comprises the attainment of the active drug with average size below 400 nm (micro particles). The authors proclaim that the use of the active drug in reduced particles make the composition, in the suspension form, easier to prepare and with increased bioavailability. This document describes the process employed to the active pharmaceutical ingredient in order to achieve these micro particles, which represents a new step in the process, making this approach expensive. Another aspect is the knowledge of the inadequate absorption and bioavailability of ritonavir when a solid composition was administered to the patient, since the ideal is a composition in which ritonavir is soluble.

Another important knowledge is that the precipitation of the less soluble polymorfic form of ritonavir is independent to the initial crystalline form employed in the preparation of the composition but dependent to the ability of the excipients involved in the composition to stabilize and prevent this undesirable precipitation.

Other references describes the preparation of solutions and pre-emulsified concentrates adjusted to the stabilization of the active ingredients for the administration in soft gelatin capsules, however none of them describes the use of ritonavir in the preparation of these compositions.

One of the objectives of the present invention is a stable pharmaceutical composition in the solution form having the active drug 5S-(5R*,8R*,10R*,11R*)]-10-hydroxy-2-methyl-5-(1-methylethyl)-1-[2-(1-methylethyl)-4-thyazolyl]-3,6-dioxo-8,11-bis(phenylmethyl)-2,4,7,12-tetraazatridecan- 13-oic acid 5-thiazolylmethyl ester, known as ritonavir, to make oral solutions or, hard or soft gelatin capsules for the oral treatment of AIDS.

Another objective of the present invention is the process for the attainment of concentrated pharmaceutical composition of 5S-(5R*,8R*,10R*,11R*)]-10-hydroxy-2-methyl-5-(1-methylethyl)-1-[2-(1-methylethyl)-4-thyazolyl]-3,6-dioxo-8,11-bis(phenylmethyl)-2,4,7,12-tetraazatridecan-13-oic acid 5-thiazolylmethyl ester (ritonavir), in order to achieve a composition with raised concentration of this active drug without previous manipulation to attainment the more soluble polymorphic form.

Currently the commercial pharmaceutical composition with 5S-(5R*,8R*,10R*,11R*)]-10-hydroxy-2-methyl-5-(1-methylethyl)-1-[2-(1-methylethyl)-4-thyazolyl]-3,6-dioxo-8,11-bis(phenylmethyl)-2,4,7,12-tetraazatridecan-13-oic acid 5-thiazolylmethyl ester (ritonavir) in the form of soft gelatin capsules needed to be administered in a daily dose of 1200 mg, distributed in two administrations of 600 mg each. The soft gelatin capsules commercially available presents 100 mg of ritonavir for each capsule. Raised concentrated compositions are not gotten because of the impossibility to stabilize this composition and prevent the precipitation of the less soluble polymorphic form, which interfere in the final bioavailability of ritonavir.

The actual therapy involves the ingestion of six capsules of ritonavir, twice a day in a total amount of 12 ingested capsules daily. The patient in treatment will ingest a total of 360 capsules in a month, admittedly an amount extremely high, mainly if we consider that the patient will ingest other components of the cocktail anti-AIDS.

The commercial composition is prepared by controlling the initial crystalline form of ritonavir, which have to be the more soluble polimorphic form in order to obtain the necessary dissolution to prepare this composition.

The raised quantity of the selected excipients in the adjusted therapy is due to the low solubility of ritonavir in these excipients and this means that each commercial capsule of ritonavir have a final weight of 1000 mg of the composition in which comprises a 100 mg dose of ritonavir. This quantity is confined in an oblong soft gelatin capsule n° 20, which presents an average length of about 22.0 mm for a diameter of 10.0 mm.

We can observe that this capsules presents raised dimensions becoming difficult the ingestion by the patients submitted to the therapy, mainly the elder's patients, the children's and the patients with several infections of the digestive tract, frequently present in the acute cases of this disease.

The pharmaceutical soluble composition of the present invention comprises the following ingredients:

1. 5S-(5R*,8R*,10R*,11R*)]-10-hydroxy-2-methyl-5-(1-methylethyl)-1-[2-(1-methylethyl)-4-thyazolyl]-3,6-dioxo-8,11-bis(phenylmethyl)-2,4,7,12-tetraazatridecan-13-oic acid 5-thiazolylmethyl ester (ritonavir);
2. A mixture of alcoholic solvent and alcoholic co-solvent from $C_2$-$C_4$.
3. A mixture of medium chain mono/diglycerides of $C_8$-$C_{10}$;
4. A non-ionic surfactant;
5. A pharmaceutical acceptable antioxidant.

Optionally the pharmaceutical composition of the present invention will also have:
(a) an emulsion stabilizer;
(b) A polarity corrector.

The active pharmaceutical ingredient employed in this composition is 5S-(5R*,8R*,10R*,11R*)]-10-hydroxy-2-methyl-5-(1-methylethyl)-1-[2-(1-methylethyl)-4-thyazolyl]-3,6-dioxo-8,11-bis(phenylmethyl)-2,4,7,12-tetraazatridecan-13-oic acid 5-thiazolylmethyl ester (ritonavir). Ritonavir is employed in a concentration from 1% to 60% of the final weight of the composition, preferably from 10% to 50% of the final weight of the composition.

The pharmaceutical composition still comprises a mixture of alcoholic solvent and alcoholic co-solvent adjusted to prevent the precipitation of ritonavir. Among the pharmaceutical acceptable alcoholic solvents for the preparation of the present composition we find those consisting of $C_2$-$C_4$, preferably a mixture of ethanol (solvent) and propylene glycol (co-solvent). The amount of ethanol employed in the composition is believed to be from 5,0% w/w to about 20% w/w, more preferably in a concentration of 5,0% w/w to about 15% w/w of the final composition, while the amount of propylene glycol employed in the composition is believed to be from 5,0% w/w to about 20% w/w, more preferably in a concentration of 5,0% w/w to about 15% w/w of the final composition. The mixture alcoholic solvent and co-solvent are in a concentration varying from 10% to 30% in weight of the final composition.

The pharmaceutical composition of the present invention also comprises a mixture of mono/diglycerides with an average chain $C_8$-$C_{10}$, which have the ability to increase the bioavailability of drugs that presents low solubility. Their activity is expressed through an efficient dissolution and dispersion of the active ingredient and also expressed directly in the barrier of epithelial cells of the gastrointestinal tract improving the absorption and the transport of the active ingredient through this barrier. These mixtures of mono/diglycerides with average chain are commercially available, among them Akoline MCM which present highest pureness and acceptable pharmaceutical quality for the preparation of the composition of the present invention. In the composition of the present invention this mixture are in a concentration between 20% w/w to 80% w/w of the final composition, preferably in a concentration between 20% w/w to 70% w/w of the final composition.

The composition of the present invention may have in the formula a neutral liquid surfactant chosen between polyethoxylate castor oil derivatives, preferably the polyethoxylate castor oil 35 (for example: Cremofor EL) and the hydrogenated polyethoxylate castor oil 40 (for example: Cremofor RH 40). Another acceptable surfactants are the polyoxyethylated sorbitol fatty acids esters derivatives, known as polysorbates. In the composition of the present invention the preferably polysorbates are the liquid polysorbates 20, 40, 60 and 80, presents in a range of about 0.1% to 20% in weight of the final composition.

In order to enhance the stability of the compositions of the present invention, substances known as antioxidants can be added to avoid the decomposition or its accelerated degradation. Among suitable antioxidants used with the ingredients of the present composition special attention is given to alpha-tocopherol and butylated hydroxy toluene (BHT). In the composition of the present invention the antioxidant is used in a range from 0.001% to about 2.0% in weight of the final composition.

Optionally, in the pharmaceutical compositions of the present invention could be used polyethyleneglycol 400 (PEG 400) as an emulsion-stabilizing agent. The use of PEG 400 as stabilizing for emulsions finds its application mainly directed to systems presenting small quantities of water. The presence of a small amount of water in the compositions of the present invention may belong from solvents used, or can be added to proportionate a minimum moisture necessary to maintain the gelatin capsule within plastic suitable properties avoiding the dryness of the pellicle that surrounds the composition, which can confer friability to the capsule that can rupture by attrition. In the present invention polyethylene glycol 400 can be used in a concentration ranging from 0% to 60% in weight of the composition.

In order to guarantee higher stability against precipitation polarity corrector agents can be used. These agents are able to provide a slight polarity to the solution in order to prevent the precipitation of ritonavir. As suitable polarity corrector agents to the present invention main attention is directed to pharmaceutical acceptable acids, specially citric and ascorbic acid. The polarity correctors are employed in a concentration ranging from 0% to 0,5% in weight of the final composition.

The pharmaceutical composition described in the present invention consists of a solution in which the active ingredient ritonavir is completely dissolved. This composition is a clear, transparent oily solution with low viscosity.

The main feature of this composition is the possibility of being formulated having an elevated concentration of the active pharmaceutical ingredient ritonavir, when compared to the marketed available composition. While the concentration of the pharmaceutical composition employed with the soft gelatin capsules currently marketed is about 10% of ritonavir, the concentration of the pharmaceutical composition of the present invention is in the range of about 1.0% to 60% in weight of ritonavir in the final composition, and that means it can reach 6 times higher the concentration of the currently marketed composition.

In accordance with the present invention the pharmaceutical composition described comprises ritonavir in a concentration from 10.0 mg to 600 mg per gram of the final composition.

This improvement allows the preparation of high concentrated compositions and the administration regime for this medicine can be improved and simplified. The quantity of ingested capsules can be reduced and/or capsules can be miniaturized in order to have a more appropriate size for ingestion.

Considering that one of the main reasons for the lack of or partial adherence from patients to the therapy with protease inhibitors, especially ritonavir, is the amount of ingested capsules daily and the capsule size that is uncomfortable to ingestion, the pharmaceutical concentrate composition of the present invention shows to be an extremely favorable alternative to contributes to the adherence from patients to treatment. Due the improvement reached it is possible the administration of higher therapeutic amounts of ritonavir for each capsule administered, reducing considerably the number of capsules ingested everyday. Another alternative to augment the patient adherence to treatment is the possibility of promoting the manufacture of a capsule with a considerably reduced size, facilitating its administration to patients who posses any difficulty to ingest the large capsules available nowadays in the market.

Another objective of the present invention is the process for the attainment of such concentrate composition. The marketed ritonavir composition consists in a pharmaceutical composition where the active pharmaceutical ingredient used in its manufacturing should be employed in a controlled crystalline form and preferably free from its less soluble polymorph, in order to have a complete dissolution in the excipients chosen without submitting the composition to high temperatures, avoiding degradation from the composition ingredients. The used process in the preparation of the present concentrated composition allows working with any crystalline form of ritonavir, and there is no need to submit this active pharmaceutical ingredient to controlled crystallization processes or modification of its crystalline shape previously to the preparation of the pharmaceutical composition.

In order to privilege the use of any crystalline form for the obtainment of the pharmaceutical composition of the present invention, preferably its preparation will be effected by using a special dissolution process, different from the processes proposed in the prior references, which consists on the direct dissolution of ritonavir in the excipients used to prepare the marketed available composition.

In accordance with the above dissolution process, in order to obtain the concentrate composition of the present invention there would be necessary to work with the more soluble polymorph and additionally promote the heat of the excipients of the composition to moderate temperatures (from 45° C. to 60° C.). As the warming of the composition could be deleterious to the stability of ritonavir, it is necessary to employ a differentiated process for obtaining the concentrate soluble composition of the present invention.

The process for preparation of a concentrated pharmaceutical composition of [5S-(5R*,8R*,10R*,11R*)]-10-hydroxy-2-methyl-5-(1-methylethyl)-1-[2-(1-methylethyl)-4-thyazolyl]-3,6-dioxo-8,11-bis(phenylmethyl)-2,4,7,12-tetraazatridecan-13-oic acid 5-thiazolylmethyl ester (ritonavir) consists of the following steps:

(a2) Completely dissolution of [5S-(5R*,8R*,10R*,11R*)]-10-hydroxy-2-methyl-5-(1-methylethyl)-1-[2-(1-methylethyl)-4-thyazolyl]-3,6-dioxo-8,11-bis(phenylmethyl)-2,4,7,12-tetraazatridecan-13-oic acid 5-thiazolylmethyl ester (ritonavir), in a sufficient amount of the alcoholic solvent from $C_2$-$C_4$, under controlled temperature;

(b2) Elimination of solid particles by means of filtration;

(c2) Evaporation the alcoholic solvent, under reduced pressure at low temperatures to about half the initial concentration;

(d2) Addition the alcoholic co-solvent, the medium chain mono/diglyceride mixture, the antioxidant, the emulsion-stabilizing agent and the polarity corrector in the appropriate amounts for the composition;

(e2) Removing the alcoholic solvent by distilling under reduced pressure until the remaining quantity is the desired quantity in the composition;

(f2) Adding the surfactant under continuous stirring and maintain stirring until mixture is complete.

(g2) If necessary, correct the weight of the final composition by the addition of the alcoholic solvent employed in the initial dissolution of ritonavir.

Initially ritonavir is completely dissolved in a sufficient quantity of the alcoholic solvent, preferably ethanol, in order to obtain a completely clear solution. To avoid the degradation of the active pharmaceutical ingredient, the dissolution is conducted in a temperature ranging from 30° C. to 45° C., under stirring. To guarantee the absence of solid particles that can trigger the precipitation process later, this alcoholic solution is filtered using usual filtration techniques, and the clear solution is submitted to an evaporation process of its solvent under reduced pressure at a temperature not higher than 40° C. This evaporation proceeds until about 50% of solvent volume used to dissolve ritonavir being distilled. At this moment the alcoholic co-solvent (propylene glycol), the medium chain mono/diglycerides mixture, the antioxidant (butylated hydroxy toluene or alpha-tocopherol) and eventually the emulsion stabilizing agent (polyethylene glycol 400) and the polarity corrector (citric or ascorbic acid) are added in the desired quantities needed in the final composition. After that the evaporation of the alcoholic solvent (ethanol) is performed under reduced pressure in a temperature not higher than 40° C. until its concentration in the final composition correspond to the desired quantity. To this liquid it is added the desired amount of the surfactant (polyethoxylated castor oil 35, and/or hydrogenated polyethoxylated castor oil 40, and/or polysorbate 20, 40, 60 or 80) in the composition and the liquid is kept under stirring until complete solubilization. Finally, the composition is weighted and if it is necessary to perform any correction it is done by using ethanol.

Preferably the alcoholic solvent used in the initial dissolution of ritonavir is ethanol that besides, being a part of the composition, presents a low boiling point being possible its easy removal at low temperatures by distillation or evaporation procedures under low pressure.

Through this procedure it is possible to obtain a concentrate ritonavir composition in a stable form, where the active pharmaceutical ingredient is completely soluble without the presence of microcrystalline forms or solid particles that are capable of triggering the crystallization of the less soluble polymorph with time, interfering with the ideal characteristics of absorption and bioavailability of this drug.

By this process there is no need to use the active pharmaceutical ingredient in a special crystalline form as the use of the higher soluble polymorphic form or an amorphous form, excluding the need of reprocessing the active ingredient for the preparation of pharmaceutical compositions. Additionally, through this technical advance it is possible to obtain highly concentrated compositions of ritonavir, impossible of being obtained by usual procedures of direct dissolution without considerably degradation of the composition.

The combination of the excipients constituting the composition of the present invention shows to be adequate to avoid the precipitation of ritonavir. The soluble concentrate, which corresponds to this composition obtained by the process, shows a great stability against eventual precipitation or crystallization and changes on its physical state. Even when the composition is submitted to low temperatures (2° C. to 8° C.) for prolonged periods of time there is no evidence of formation of jelly, crystalline or microcrystalline structures, which could start the precipitation or crystallization of less soluble polymorphic form of the active pharmaceutical ingredient. Such event could be harmful to the final absorption and bioavailability of this protease inhibitor that would not be completely soluble in the composition.

The stability demonstrated by the composition of the present invention against ritonavir crystallization guarantee delivering and/or liberation of the active pharmaceutical ingredient at the absorption site in a liquid soluble state suitable for a prompt absorption by the body.

Stability studies performed with the pharmaceutical composition of the present invention show consistent results regarding the maintenance of the active pharmaceutical ingredient in a soluble state suitable to its administration and to the prompt absorption of the drug by the organism.

The soluble pharmaceutical composition of the present invention can be administered as an oral solution, in this case being fractioned by fractioning suitable devices. In case of oral solutions can be added flavoring excipients, dyers, and other substances capable of mask or giving suitable taste and appearance to the composition.

In a preferential realization of the present invention, the described concentrated pharmaceutical composition is encapsulated in soft gelatin capsules, which present uniform delivery properties of their contend in the gastrointestinal tract, in addition they are better accepted by treated patients because its elastics properties conferring a smooth ingestion. Besides all these factors, administration as capsules allows a better management of the dosage avoiding the need of previous composition fractioning performed by the patient, and it proportionate a tasteless administration.

An important issue referring the administration of the present composition in the form of soft gelatin capsules is the possibility to reduce considerably the number of capsules taken and/or to reduce the final volume of the capsule. As disclosed earlier, ritonavir on its present marketed formulation must be administered to the patient in a dosage consisting in six soft gelatin capsules twice a day, constituting a total amount of 12 capsules a day. Besides the elevate number of capsules that must be constantly ingested, there is the problem related to the dimension of the capsule, which is very large representing a consistent obstacle to the adherence of the patients to therapy because it is difficult to swallow. Due the improvement reached by the present invention on hindering the crystallization of ritonavir in concentrated solutions, the amount of administered capsules can be reduced consistently and/or its size can be reduced in order to proportionate a final presentation easier to swallow to treated patients.

By using the composition of the present invention it is possible to produce soft gelatin capsules capable of delivering amounts of 200 mg of ritonavir by capsule or even 300 mg of ritonavir by capsule, which would reduce the dosage administration for 6 or even 4 capsules a day. This significant alteration in the regimen of administration of this drug will strongly contribute to enhance the adherence of patients submitted to the therapy, providing a simplified usage regime and disentailed from taking large amounts of capsules from this medicine for virus suppression.

The technique used in the preparation of the soft gelatin capsules is well known, basically consisting on employing gelatin, plastifying agents and water in defined proportions. Additionally the capsule material may contain additives like dyers, pigments and flavoring agents among others ingredients. Several techniques may be used for the preparation of soft gelatin capsules. As an example, its manufacture may consist on a process with or without sews, rotary processing, using specific machinery, among others. As an example the soft gelatin capsules prepared as a shell for the concentrated pharmaceutical composition of the present invention may consist of gelatin, glycerol as plastifying agent, propylparabene, titanium dioxide, water, dying substances and be prepared by conventional technique.

In general way the present invention composition can be submitted to any existing process for the manufacture of soft gelatin capsules, since it does not considerably interfere on its composition, or it means, on its production process does not happen significant change among its ingredients by evaporation due to high temperatures, drying processes, or any other kind of processing.

The following examples are illustrative but not exhaustive about the possibilities of the present invention and its preparation procedure, as well they demonstrate its stability and the maintaining of its original properties as a soluble ritonavir concentrate for long periods of time.

General procedure for the preparation of concentrated pharmaceutical composition:

The compositions of the present invention may be prepared in accordance with the following procedure. Ritonavir was dissolved in an enough amount of ethanol to its complete dissolution at a temperature between 30 and 45° C. The clear ethanolic solution was filtered and transferred to a vacuum rotary evaporator, where ethanol was distilled under reduced pressure at a temperature of about 40° C., until half of the total ethanol contend was removed. Once reduced the amount of ethanol, the organic co-solvent (propylene glycol), the medium chain mono/diglycerides, the antioxidant and the eventual emulsion stabilizing agent and polarity corrector agent were added to the system. The system remained under stirring until the mixture became a clear solution. The surfactant was then added and the system was kept under stirring until the mixture became a clear solution. The weight of the solution was measured and in the eventual need to correct the weight of the final composition ethanol was used to correct its weight.

Accordingly to this procedure the following examples were prepared:

EXAMPLE 1

| Ingredient | Weight percent |
|---|---|
| Ritonavir | 20.00 |
| Ethanol | 12.00 |
| Propylene glycol | 10.00 |
| Medium chain mono/diglycerides (AKOLINE MCM) | 50.980 |
| Butylated hydroxy toluene (BHT) | 0.025 |
| Polyethoxylated castor oil 35 | 6.00 |
| Water | 0.995 |

The composition described above was divided into two portions, one of them filled into soft gelatin capsules in a quantity of 500 mg/capsule conferring a ritonavir dose of 100 mg/capsule, and the other portion was filled into soft gelatin capsules in a quantity of 1,000 mg/capsule containing 200 mg of ritonavir/capsule.

EXAMPLE 2

| Ingredient | Weight percent |
|---|---|
| Ritonavir | 20.00 |
| Ethanol | 12.00 |
| Propylene glycol | 10.00 |
| Medium chain Mono/diglycerides (AKOLINE MCM) | 51.975 |
| Butylated hydroxy toluene (BHT) | 0.025 |
| Polyethoxylated castor oil 35 | 6.00 |

The composition described above was divided into two portions, one of them filled into soft gelatin capsules in a quantity of 500 mg/capsule conferring a ritonavir dose of 100 mg/capsule, and the other portion was filled into soft gelatin capsules in a quantity of 1,000 mg/capsule containing 200 mg of ritonavir/capsule.

EXAMPLE 3

| Ingredient | Weight percent |
|---|---|
| Ritonavir | 20.00 |
| Ethanol | 12.00 |
| Propylene glycol | 10.00 |
| Medium chain mono/diglycerides (AKOLINE MCM) | 51.950 |
| Butilated hydroxy toluene (BHT) | 0.050 |
| Polyethoxylated castor oil 35 | 6.000 |

The composition described above was divided into two portions, one of them filled into soft gelatin capsules in a quantity of 500 mg/capsule conferring a ritonavir dose of 100 mg/capsule, and the other portion was filled into soft gelatin capsules in a quantity of 1,000 mg/capsule containing 200 mg of ritonavir/capsule.

EXAMPLE 4

| Ingredient | Weight percent |
|---|---|
| Ritonavir | 20.00 |
| Ethanol | 12.00 |
| Propylene glycol | 10.00 |
| Medium chain mono/diglycerides (AKOLINE MCM) | 50.955 |
| Butylated hydroxy toluene (BHT) | 0.050 |
| Polyethoxylated castor oil 35 | 6.000 |
| Water | 0.995 |

The composition described above was divided into two portions, one of them filled into soft gelatin capsules in a quantity of 500 mg/capsule conferring a ritonavir dose of 100 mg/capsule, and the other portion was filled into soft gelatin capsules in a quantity of 1,000 mg/capsule containing 200 mg of ritonavir/capsule.

EXAMPLE 5

| Ingredient | Weight percent |
|---|---|
| Ritonavir | 20.00 |
| Ethanol | 12.00 |
| Propylene glycol | 10.00 |
| Medium chain mono/diglycerides (AKOLINE MCM) | 23.4875 |
| Polyethylene glycol 400(Peg 400) | 23.4875 |
| Butylated hydroxy toluene (BHT) | 0.025 |
| Polyethoxylated castor oil 35 | 10.00 |
| Water | 1.000 |

The composition described above was divided into two portions, one of them filled into soft gelatin capsules in a quantity of 500 mg/capsule conferring a ritonavir dose of 100 mg/capsule, and the other portion was filled into soft gelatin capsules in a quantity of 1,000 mg/capsule containing 200 mg of ritonavir/capsule.

EXAMPLE 6

| Ingredient | Weight percent |
|---|---|
| Ritonavir | 20.00 |
| Ethanol | 12.00 |
| Propylene glycol | 10.00 |
| Medium chain mono/diglycerides (AKOLINE MCM) | 23.475 |
| Polyethylene glycol 400(Peg 400) | 23.475 |
| Butylated hydroxy toluene (BHT) | 0.050 |
| Polyethoxylated castor oil 35 | 10.00 |
| Water | 1.000 |

The composition described above was divided into two portions, one of them filled into soft gelatin capsules in a quantity of 500 mg/capsule conferring a ritonavir dose of 100 mg/capsule, and the other portion was filled into soft gelatin capsules in a quantity of 1,000 mg/capsule containing 200 mg of ritonavir/capsule.

EXAMPLE 7

| Ingredient | Weight percent |
| --- | --- |
| Ritonavir | 20.00 |
| Ethanol | 12.00 |
| Propylene glycol | 10.00 |
| Medium chain mono/diglycerides (AKOLINE MCM) | 51.875 |
| Butylated hydroxy toluene (BHT) | 0.025 |
| Polyethoxylated castor oil 35 | 6.000 |
| Citric acid | 0.100 |

The composition described above was divided into two portions, one of them filled into soft gelatin capsules in a quantity of 500 mg/capsule conferring a ritonavir dose of 100 mg/capsule, and the other portion was filled into soft gelatin capsules in a quantity of 1,000 mg/capsule containing 200 mg of ritonavir/capsule.

EXAMPLE 8

| Ingredient | Weight percent |
| --- | --- |
| Ritonavir | 20.00 |
| Ethanol | 12.00 |
| Propylene glycol | 10.00 |
| Medium chain mono/diglycerides (AKOLINE MCM) | 51.850 |
| Butylated hydroxy toluene (BHT) | 0.050 |
| Polyethoxylated castor oil 35 | 6.000 |
| Citric acid | 0.100 |

The composition described above was divided into two portions, one of them filled into soft gelatin capsules in a quantity of 500 mg/capsule conferring a ritonavir dose of 100 mg/capsule, and the other portion was filled into soft gelatin capsules in a quantity of 1,000 mg/capsule containing 200 mg of ritonavir/capsule.

EXAMPLE 9

| Ingredient | Weight percent |
| --- | --- |
| Ritonavir | 20.00 |
| Ethanol | 12.00 |
| Propylene glycol | 10.00 |
| Medium chain mono/diglycerides (AKOLINE MCM) | 50.875 |
| Butylated hydroxy toluene (BHT) | 0.025 |
| Polyethoxylated castor oil 35 | 6.000 |
| Citric acid | 0.100 |
| Water | 1.000 |

The composition described above was divided into two portions, one of them filled into soft gelatin capsules in a quantity of 500 mg/capsule conferring a ritonavir dose of 100 mg/capsule, and the other portion was filled into soft gelatin capsules in a quantity of 1,000 mg/capsule containing 200 mg of ritonavir/capsule.

EXAMPLE 10

| Ingredient | Weight percent |
| --- | --- |
| Ritonavir | 20.00 |
| Ethanol | 12.00 |
| Propylene glycol | 10.00 |
| Medium chain mono/diglycerides (AKOLINE MCM) | 50.850 |
| Butylated hydroxy toluene (BHT) | 0.050 |
| Polyethoxylated castor oil 35 | 6.000 |
| Citric acid | 0.100 |
| Water | 1.000 |

The composition described above was divided into two portions, one of them filled into soft gelatin capsules in a quantity of 500 mg/capsule conferring a ritonavir dose of 100 mg/capsule, and the other portion was filled into soft gelatin capsules in a quantity of 1,000 mg/capsule containing 200 mg of ritonavir/capsule.

EXAMPLE 11

| Ingredient | Weight percent |
| --- | --- |
| Ritonavir | 20.0 |
| Ethanol | 12.0 |
| Propylene glycol | 10.0 |
| Medium chain Mono/diglycerides (AKOLINE MCM) | 23.9375 |
| Polyethylene glycol 400 (PEG 400) | 23.9375 |
| Butylated hydroxy toluene (BHT) | 0.025 |
| Polyethoxylated castor oil 35 | 10.0 |
| Citric acid | 0.1 |

The composition described above was divided into two portions, one of them filled into soft gelatin capsules in a quantity of 500 mg/capsule conferring a ritonavir dose of 100 mg/capsule, and the other portion was filled into soft gelatin capsules in a quantity of 1,000 mg/capsule containing 200 mg of ritonavir/capsule.

EXAMPLE 12

| Ingredient | Weight percent |
| --- | --- |
| Ritonavir | 20.0 |
| Ethanol | 12.0 |
| Propylene glycol | 10.0 |
| Medium chain Mono/diglycerides (AKOLINE MCM) | 23.925 |
| Polyethylene glycol 400 (PEG 400) | 23.925 |
| Butylated hydroxy toluene (BHT) | 0.050 |
| Polyethoxylated castor oil 35 | 10.0 |
| Citric acid | 0.1 |

The composition described above was divided into two portions, one of them filled into soft gelatin capsules in a quantity of 500 mg/capsule conferring a ritonavir dose of 100 mg/capsule, and the other portion was filled into soft gelatin capsules in a quantity of 1,000 mg/capsule containing 200 mg of ritonavir/capsule.

EXAMPLE 13

| Ingredient | Weight percent |
|---|---|
| Ritonavir | 20.00 |
| Ethanol | 12.00 |
| Propylene glycol | 10.00 |
| Medium chain Mono/diglycerides (AKOLINE MCM) | 26.4375 |
| Polyethylene glycol 400 (PEG 400) | 26.4375 |
| Butylated hydroxy toluene (BHT) | 0.025 |
| Polyethoxylated castor oil 35 | 5.000 |
| Ascorbic acid | 0.100 |

The composition described above was divided into two portions, one of them filled into soft gelatin capsules in a quantity of 500 mg/capsule conferring a ritonavir dose of 100 mg/capsule, and the other portion was filled into soft gelatin capsules in a quantity of 1,000 mg/capsule containing 200 mg of ritonavir/capsule.

EXAMPLE 14

| Ingredient | Weight percent |
|---|---|
| Ritonavir | 20.00 |
| Ethanol | 12.00 |
| Propylene glycol | 10.00 |
| Medium chain Mono/diglycerides (AKOLINE MCM) | 25.9375 |
| Polyethylene glycol 400 (PEG 400) | 25.9375 |
| Butylated hydroxy toluene (BHT) | 0.025 |
| Polyethoxylated castor oil 35 | 5.000 |
| Ascorbic acid | 0.100 |
| Water | 1.000 |

The composition described above was divided into two portions, one of them filled into soft gelatin capsules in a quantity of 500 mg/capsule conferring a ritonavir dose of 100 mg/capsule, and the other portion was filled into soft gelatin capsules in a quantity of 1,000 mg/capsule containing 200 mg of ritonavir/capsule.

EXAMPLE 15

| Ingredient | Weight percent |
|---|---|
| Ritonavir | 20 |
| Ethanol | 12 |
| Propylene glycol | 10 |
| Medium chain Mono/diglycerides (AKOLINE MCM) | 45.7775 |
| Polyethylene glycol 400 (PEG 400) | 5.1975 |
| Butylated hydroxy toluene (BHT) | 0.025 |
| Polyethoxylated castor oil 35 | 6.000 |

The composition described above was divided into two portions, one of them filled into soft gelatin capsules in a quantity of 500 mg/capsule conferring a ritonavir dose of 100 mg/capsule, and the other portion was filled into soft gelatin capsules in a quantity of 1,000 mg/capsule containing 200 mg of ritonavir/capsule.

EXAMPLE 16

| Ingredient | Weight percent |
|---|---|
| Ritonavir | 20 |
| Ethanol | 12 |
| Propylene glycol | 10 |
| Medium chain Mono/diglycerides (AKOLINE MCM) | 45.8775 |
| Polyethylene glycol 400 (PEG 400) | 5.0975 |
| Butilated hydroxy toluene (BHT) | 0.025 |
| Polyethoxylated castor oil 35 | 6.000 |
| Water | 1.000 |

The composition described above was divided into two portions, one of them filled into soft gelatin capsules in a quantity of 500 mg/capsule conferring a ritonavir dose of 100 mg/capsule, and the other portion was filled into soft gelatin capsules in a quantity of 1,000 mg/capsule containing 200 mg of ritonavir/capsule.

EXAMPLE 17

| Ingredient | Weight percent |
|---|---|
| Ritonavir | 30 |
| Ethanol | 12 |
| Propylene glycol | 10 |
| Medium chain Mono/diglycerides (AKOLINE MCM) | 40.925 |
| Butylated hydroxy toluene (BHT) | 0.075 |
| Polyethoxylated castor oil 35 | 6.000 |
| Water | 1.000 |

The composition described above was divided into two portions, one of them filled into soft gelatin capsules in a quantity of 500 mg/capsule conferring a ritonavir dose of 150 mg/capsule, and the other portion was filled into soft gelatin capsules in a quantity of 1,000 mg/capsule containing 300 mg of ritonavir/capsule.

EXAMPLE 18

| Ingredient | Weight percent |
|---|---|
| Ritonavir | 30 |
| Ethanol | 12 |
| Propylene glycol | 10 |
| Medium chain Mono/diglycerides (AKOLINE MCM) | 41.925 |
| Butylated hydroxy toluene (BHT) | 0.075 |
| Polyethoxylated castor oil 35 | 6.000 |

The composition described above was divided into two portions, one of them filled into soft gelatin capsules in a quantity of 500 mg/capsule conferring a ritonavir dose of 150 mg/capsule, and the other portion was filled into soft gelatin capsules in a quantity of 1,000mg/capsule containing 300 mg of ritonavir/capsule.

EXAMPLE 19

| Ingredient | Weight percent |
|---|---|
| Ritonavir | 30 |
| Ethanol | 12 |
| Propylene glycol | 10 |
| Medium chain Mono/diglycerides (AKOLINE MCM) | 36.8325 |
| Polyethylene glycol 400(PEG 400) | 4.0925 |
| Butylated hydroxy toluene (BHT) | 0.075 |
| Polyethoxylated castor oil 35 | 6.000 |
| Water | 1.000 |

The composition described above was divided into two portions, one of them filled into soft gelatin capsules in a quantity of 500 mg/capsule conferring a ritonavir dose of 150 mg/capsule, and the other portion was filled into soft gelatin capsules in a quantity of 1,000 mg/capsule containing 300 mg of ritonavir/capsule.

EXAMPLE 20

| Ingredient | Weight percent |
|---|---|
| Ritonavir | 30 |
| Ethanol | 12 |
| Propylene glycol | 10 |
| Medium chain Mono/diglycerides (AKOLINE MCM) | 33.2325 |
| Polyethylene glycol 400(PEG 400) | 3.6925 |
| Butylated hydroxy toluene (BHT) | 0.075 |
| Polyethoxylated castor oil 35 | 10.000 |
| Water | 1.000 |

The composition described above was divided into two portions, one of them filled into soft gelatin capsules in a quantity of 500 mg/capsule conferring a ritonavir dose of 150 mg/capsule, and the other portion was filled into soft gelatin capsules in a quantity of 1,000 mg/capsule containing 300 mg of ritonavir/capsule.

EXAMPLE 21

| Ingredient | Weight percent |
|---|---|
| Ritonavir | 10 |
| Ethanol | 12 |
| Propylene glycol | 10 |
| Medium chain mono/diglycerides (AKOLINE MCM) | 60.9875 |
| Butylated hydroxy toluene (BHT) | 0.0125 |
| Polyethoxylated castor oil 35 | 6.000 |
| Water | 1.000 |

The composition described above was divided into two portions, one of them filled into soft gelatin capsules in a quantity of 500 mg/capsule conferring a ritonavir dose of 50 mg/capsule, and the other portion was filled into soft gelatin capsules in a quantity of 1,000 mg/capsule containing 100 mg of ritonavir/capsule.

EXAMPLE 22

| Ingredient | Weight percent |
|---|---|
| Ritonavir | 10 |
| Ethanol | 12 |
| Propylene glycol | 10 |
| Medium chain Mono/diglycerides (AKOLINE MCM) | 15.5 |
| Polyethylene glycol 400(PEG 400) | 46.4875 |
| Butylated hydroxy toluene (BHT) | 0.0125 |
| Polyethoxylated castor oil 35 | 6.000 |

The composition described above was divided into two portions, one of them filled into soft gelatin capsules in a quantity of 500 mg/capsule conferring a ritonavir dose of 50 mg/capsule, and the other portion was filled into soft gelatin capsules in a quantity of 1,000 mg/capsule containing 100 mg of ritonavir/capsule.

EXAMPLE 23

| Ingredient | Weight percent |
|---|---|
| Ritonavir | 10 |
| Ethanol | 12 |
| Propylene glycol | 10 |
| Medium chain mono/diglycerides (AKOLINE MCM) | 30.4875 |
| Polyethylene glycol 400(PEG 400) | 30.500 |
| Butylated hydroxy toluene (BHT) | 0.0125 |
| Polyethoxylated castor oil 35 | 6.000 |
| Water | 1.000 |

The composition described above was divided into two portions, one of them filled into soft gelatin capsules in a quantity of 500 mg/capsule conferring a ritonavir dose of 50 mg/capsule, and the other portion was filled into soft gelatin capsules in a quantity of 1,000 mg/capsule containing 100 mg of ritonavir/capsule.

EXAMPLE 24

| Ingredient | Weight percent |
|---|---|
| Ritonavir | 10 |
| Ethanol | 12 |
| Propylene glycol | 10 |
| Medium chain Mono/diglycerides (AKOLINE MCM) | 48.710 |
| Polyethylene glycol 400(PEG 400) | 12.1775 |
| Butylated hydroxy toluene (BHT) | 0.0125 |
| Polyethoxylated castor oil 35 | 6.000 |
| Citric acid | 0.100 |
| Water | 1.000 |

The composition described above was divided into two portions, one of them filled into soft gelatin capsules in a quantity of 500mg/capsule conferring a ritonavir dose of 50 mg/capsule, and the other portion was filled into soft gelatin capsules in a quantity of 1,000 mg/capsule containing 100 mg of ritonavir/capsule.

Pharmaceutical compositions of the present invention were submitted to the following stability evaluating conditions. Accordingly with the studies protocol, any deviation obtained above the established parameters for its quality was indicative of its non-stability at the previously established condition for the study.

STUDY 1:

Soft gelatin capsules filled with the pharmaceutical composition of the present invention were submitted to stability study at room temperature (25° C.±2° C., relative humidity of 60% ±5%). For the evaluation of the stability, were performed tests for appearance of the solution, assay, individual and total impurities, among others. The ongoing stability study at this condition completed 6 months. An amber glass vial with the composition was kept under the same conditions of the study as control.

STUDY 2:

Soft gelatin capsules filled with the pharmaceutical composition of the present invention were submitted to accelerated stability study (40° C.±2° C., relative humidity of 75%±5%). For the evaluation of the stability, were performed tests for appearance of the solution, assay, individual and total impurities, among others. The ongoing stability study at this condition completed 6 months. An amber glass vial with the composition was kept under the same conditions of the study as control.

STUDY 3:

Soft gelatin capsules filled with the pharmaceutical composition of the present invention were submitted to crystallization study under refrigeration (5° C.±3° C.). The objective of this study is to monitor the precipitation of ritonavir in the concentrated compositions at low temperatures condition that accelerates the formation of crystals in nom-stabilized compositions. An amber glass vial with the composition was kept under the same conditions of the study as control.

RESULTS

All preparations presented suitable results in the tests submitted. The table below summarizes some of the studied batches as demonstration:

| Example | Study Condition | Assay | Individual Impurity | Total Impurity | Appearance |
|---|---|---|---|---|---|
| 1 | TA | Initial = 99.76% Final = 99.73% | Initial = 0.01% Final = 0.01% | Initial = 0.01% Final = 0.01% | Initial = Clear solution Final = Clear solution |
| 1 | AC | Initial = 99.76% Final = 98.38% | Initial = 0.01% Final = 0.03% | Initial = 0.01% Final = 0.04% | Initial = Clear solution Final = Clear solution |
| 1 | REF | Initial = 99.76% Final = 99.54% | Initial = 0.01% Final = 0.01% | Initial = 0.01% Final = 0.01% | Initial = Clear solution Final = Clear solution |
| 5 | TA | Initial = 99.91% Final = 99.79% | Initial = 0.02% Final = 0.02% | Initial = 0.02% Final = 0.03% | Initial = Clear solution Final = Clear solution |
| 5 | AC | Initial = 99.91% Final = | Initial = 0.02% Final = | Initial = 0.02% Final = | Initial = Clear Solution Final = |
| 5 | REF | 97.88% Initial = 99.91% Final = | 0.08% Initial = 0.02% Final = | 0.12% Initial = 0.02% Final = | Clear Solution Initial = Clear Solution Final = |
| 10 | TA | 99.85% Initial = 98.19% Final = 98.22% | 0.02% Initial = 0.09% Final = 0.10% | 0.02% Initial = 0.16% Final = 0.15% | Clear Solution Initial = Clear Solution Final = Clear Solution |
| 10 | AC | Initial = 98.19% Final = 96.98% | Initial = 0.09% Final = 0.11% | Initial = 0.16% Final = 0.21% | Initial = Clear Solution Final = Clear Solution |
| 10 | REF | Initial = 98.19% Final = 98.18% | Initial = 0.09% Final = 0.09% | Initial = 0.16% Final = 0.18% | Initial = Clear Solution Final = Clear Solution |

TA = Room temperature;
AC = Accelerated Study;
REF = Under Refrigeration.

The analytical tests to which samples were submitted until the present moment demonstrates that all compositions tested are within the acceptable approving parameters. The accelerated stability studies conducted with the pharmaceutical compositions of the present invention demonstrate that they are stable in the test conditions. During the stability evaluation period there was no significant change in the parameters analyzed. The assay remain within the initial specification as well as the impurity contend, individual and total, which demonstrates no significant changes during the period of the study.

The compositions remaining under low temperature do not present any alteration in the physical state, gel formation or the presence of crystals or microcrystalline solids. The only observed alteration was the higher viscosity of the composition under refrigeration, but not enough to cause significant changes in the several tests to which the compositions were submitted.

The invention claimed is:

1. A process for preparing a pharmaceutical composition of ritonavir comprising the following steps:
   (a) dissolving from 10% to 30% by weight of the final pharmaceutical composition of ritonavir in sufficient amount of an alcohol solvent of $C_2$-$C_4$ to obtain a clear solution, at a temperature between 30° C. and 45° C. to make a first mixture;
   (b) eliminating particles from said first mixture by filtration;
   (c) evaporating the alcoholic solvent from the filtered first mixture under reduced pressure at a temperature not higher than 40° C. to about half of its initial volume;
   (d) adding to the filtered and concentrated first mixture an alcoholic co-solvent in an amount of 10% by weight of the final pharmaceutical composition, a medium chain mono/diglycerides mixture in an amount ranging from 20% to 40% by weight of the final pharmaceutical composition, an antioxidant in an amount ranging from 0.01% to 0.1% by weight of the final pharmaceutical composition, an emulsion-stabilizing agent in an amount up to 60% by weight of the final pharmaceutical composition and a polarity corrector in an amount up to 0.5% by weight of the final pharmaceutical composition to make a second mixture;

(e) removing the alcoholic solvent of step (a) from said second mixture by distilling under reduced pressure to correct the weight of said second mixture until the remaining quantity of alcoholic solvent is of 12% by weight of the final pharmaceutical composition;

(f) adding to the distilled second mixture a surfactant in an amount ranging from 5% to 10% by weight of the final pharmaceutical composition under continuous stirring, until the second mixture becomes a clear solution, thereby obtaining a stable and concentrated ritonavir pharmaceutical composition; and (g) correcting, if necessary, the final weight of the final pharmaceutical pharmaceutical composition by adding the alcoholic solvent employed in the step (a) to obtain a solution comprising from 10% to 30% by weight of the final pharmaceutical composition of ritonavir.

2. The process in accordance with claim 1, wherein the alcoholic solvent used in step (a) is ethanol.

3. The process in accordance with claim 1, wherein the co-solvent employed in step (d) is propylene glycol.

4. The process in accordance with claim 1, wherein the antioxidant employed in step (d) is butylated hydroxy toluene or alpha-tocopherol.

5. The process in accordance with claim 1, wherein the emulsion-stabilizing employed in step (d) is polyethylene glycol 400 (PEG 400).

6. The process in accordance with claim 1, wherein the polarity corrector employed in step (d) is citric acid or ascorbic acid.

7. The process in accordance with claim 1, wherein the surfactant employed in step (f) is polyethoxylated castor oil 35, polyethoxylated hydrogenated castor oil 40, polysorbate 20, polysorbate 40, polysorbate 60, polysorbate 80 or a mixture of at least two thereof.

8. A stable pharmaceutical composition of ritonavir prepared by the process of claim 1, comprising:
   ritonavir in an amount ranging from 10% to 30% by weight of the final pharmaceutical composition;
   alcoholic solvent in an amount of 12% by weight of the final pharmaceutical composition;
   alcoholic co-solvent of $C_2$-$C_4$ in an amount of 10 % by weight of the final pharmaceutical composition;
   a mixture of $C_8$-$C_{10}$ medium chain mono/diglycerides in an amount ranging from 20% to 40% by weight of the final pharmaceutical composition;
   a pharmaceutically suitable surfactant in an amount ranging from 5% to 10% by weight of the final pharmaceutical composition;
   an antioxidant in an amount ranging from 0.01% to 0.1% by weight of the final pharmaceutical composition.

9. The pharmaceutical composition in accordance with claim 8, which further comprises:
   an emulsion-stabilizing agent in an amount ranging up to 60% by weight of the final pharmaceutical composition;
   a polarity corrector agent in an amount up to 0.5% by weight of the final pharmaceutical composition.

10. The pharmaceutical composition in accordance with claim 8, wherein the alcoholic solvent is ethanol and the alcoholic co-solvent is propylene glycol.

11. The pharmaceutical composition in accordance with claim 8, wherein the surfactant is polyethoxylated castor oil 35, polyethoxylated hydrogenated castor oil 40, polysorbate 20, polysorbate 40, polysorbate 60 or a mixture of at least two thereof.

12. The pharmaceutical composition in accordance with claim 8, wherein the antioxidant is butylated hydroxy toluene or alpha-tocopherol.

13. The pharmaceutical composition in accordance with claim 9, wherein the emulsion-stabilizing agent is polyethylene glycol 400 (PEG 400).

14. The pharmaceutical composition in accordance with claim 9, wherein the polarity corrector agent is citric acid or ascorbic acid.

* * * * *